United States Patent [19]

Wretlind et al.

[11] Patent Number: 5,244,925
[45] Date of Patent: Sep. 14, 1993

[54] EMULSION FOR PARENTERAL ADMINISTRATION

[75] Inventors: Karl A. J. Wretlind, Stockholm; Bengt M. Ajaxon, Uppsala, both of Sweden

[73] Assignee: Kabi Pharmacia Aktiebolag, Stockholm, Sweden

[21] Appl. No.: 771,862

[22] PCT Filed: Dec. 1, 1988

[86] PCT No.: PCT/SE88/00680
§ 371 Date: Aug. 1, 1989
§ 102(e) Date: Aug. 1, 1989

[87] PCT Pub. No.: WO89/05638
PCT Pub. Date: Jun. 29, 1989

Related U.S. Application Data

[63] Continuation of Ser. No. 382,664, Aug. 1, 1989, abandoned.

[30] Foreign Application Priority Data

Dec. 18, 1987 [SE] Sweden .............................. 8705064

[51] Int. Cl.$^5$ .............................................. A61K 47/00
[52] U.S. Cl. .................................. 514/777; 514/785; 514/786; 514/943
[58] Field of Search ............... 514/784, 788, 549, 552, 514/785, 777, 786, 943

[56] References Cited

U.S. PATENT DOCUMENTS

| | | | |
|---|---|---|---|
| 4,252,827 | 2/1981 | Yokoyama et al. | 514/943 |
| 4,284,630 | 8/1981 | Yu et al. | 514/788 |
| 4,404,182 | 9/1983 | Vermess et al. | 424/5 |
| 4,816,247 | 3/1989 | Desai et al. | 514/943 |
| 4,840,970 | 6/1989 | Ohasi et al. | 514/690 |

FOREIGN PATENT DOCUMENTS 2139889 11/1984 United Kingdom .

OTHER PUBLICATIONS

The Merck Index 10th ed. (1983) cites 6706 (pp. 979-980) and 8308 (p. 1217).
Chemical Abstracts 97(20):168842c Morimoto et al. (1982).

*Primary Examiner*—Frederick E. Waddell
*Assistant Examiner*—Raymond J. Henley, III
*Attorney, Agent, or Firm*—Pollock, Vande Sande & Priddy

[57] ABSTRACT

The invention relates to emulsions intended for parenteral administration and contaning a hydrophobic phase emulsified in a an aqueous phase. In accordance with the invention, a substantial part of the hydrophobic phase contains one or more alkyl esters of pharmacologically acceptable fatty acids, and particularly their ethyl esters. The emulsions can be used for parenteral nutrient supply and as vehicles for pharmacologically active substances or agents and may also be used for both purposes in combination.

13 Claims, No Drawings

EMULSION FOR PARENTERAL ADMINISTRATION

This application is a continuation of Ser. No. 07/382,664, filed on Aug. 1, 1989, now abandoned.

Fat emulsions which are intended, inter alia, for intravenous, nutrient supply and which exhibit insignificant secondary effects have been available since the beginning of the 1960's (Wretlind, A. Development of fat emulsions, JPEN 5: No. 3, 230.235, 1981). This development work has investigated the effect of emulsions which contain a number of mutually different fats (olive oil, cottonseed oil, soyabean oil, maize oil, safflower oil, coconut oil, etc.) and several mutually different emulsifiers (soyabean phospholipids, egg yolk phospholipids, cerebrosides, diglycerides etc.). One characteristic feature common to all of these emulsions is that the fats or oils used comprise triglycerides of fatty acids.

All of the fat emulsions earlier investigated and present day fat emulsions require preparation by homogenization under high pressure. One reason for this is because the fats used have high viscosities. Another drawback with present day fat emulsions is that the fats or oils used can only be cleansed with great difficulty, in a manner to free the glycerides completely from all other substances, such as sterols and unsaponifiable fractions. Several methods have been proposed for cleansing the oils used. One such method has been described by S. S. Chang (U.S. application Ser. No. 4, 101,673). The method to Chang involves removing a part of the polar, undesirable constituents with the aid of silica gel. Other attempts have been made with the aid of molecular distillation techniques. This latter method has not been found to have any practical value, however.

Consequently, there is a desire in this respect to find compounds other than triglycerides which will enable fatty acids to be administered in the form of emulsions, and optionally in the form of emulsions which are totally free from the so-called unsaponifiable residues present in fats of animal and vegetable origins. Another desire is one of discovering fatty acid compounds which have a lower viscosity than the lipids used hitherto and at present in the preparation of fat emulsions. A lower viscosity would also enable fat emulsions to be prepared in a somewhat simpler fashion, and would also enable emulsions to be prepared with smaller particle sizes of the colloidal suspension than those of conventionally prepared fat emulsions.

The present invention now makes it possible to prepare emulsions which will satisfy the aforesaid desiderata, with the use of alkyl esters, and then preferably ethyl esters of fatty acids deriving from synthetic, animal or vegetable origins. These alkyl esters can be obtained by esterification of triglycerides with ethyl alcohol or other alcohols in the presence of a catalyst, such as sodium alcoholate and certain zinc compounds. Alternatively, fatty acids can be prepared by complete hydrolysis of triglycerides with sodium hydroxide or potassium hydroxide, whereafter the solution containing the salt compound of the fatty acids is extracted with hexane or some other organic solvent, so as to remove unsaponifiable residues. The free fatty acids are obtained subsequent to adding hydrochloric acid or some other acid. The free fatty acids can then be converted to ethyl esters or some other alkyl esters in some suitable way, by treating the fatty acids with ethyl alcohol or some other alkyl alcohol having one or two hydroxyl groups capable of esterification. Suitable esters can also be obtained by esterifying synthetic or otherwise produced fatty acids having an even or an odd number of carbon atoms.

The present invention thus relates to an emulsion intended for parenteral administration and including a hydrophobic phase emulsified in a water phase, this emulsion being characterized in that a substantial part of the hydrophobic phase comprises one or more alkyl esters of pharmacologically acceptable fatty acids. The alkyl esters will preferably comprise low-molecular alkyl esters having 2-4 carbon atoms in the alkyl groups, and then primarily ethyl esters.

The fatty acids are preferably of vegetable, animal or synthetic origins, and will preferably have from 9 to 22 carbon atoms in their carbon chains.

In accordance with one embodiment, the carbon chain of the fatty acids will contain predominantly or exclusively an even or odd number of carbon atoms. This has been found significant with respect to certain usages of the emulsions prepared. For instance, fatty acids having an odd number of carbon atoms will produce a high percentage of glucose when metabolized, a fact which can have significance when using the emulsion for nutrient administration.

The alkyl ester content of the emulsion will suitably be from 5 to 60 percent by weight, calculated on the total emulsion, and preferably from 5 to 30 percent by weight. Future reference to percentages made in this description and appended claims refers to weight-/volume percent (w/v), unless otherwise stated.

The hydrophobic phase of the emulsion may also include glyceryl esters of fatty acids. The weight ratio of the alkyl esters to the glyceryl esters will then suitably be from 10:1 to 1:10.

The use of ethyl esters or other alkyl esters of fatty acids will afford, inter alia, the following advantages:
1:o homogenization is simplified as a result of the lower viscosity;
2:o the lower viscosity will also result in a lower viscosity of the prepared emulsion;
3:o a lower intrinsic weight, thereby enabling a lower specific weight to be obtained with, e.g., iodo-emulsions or hydroflurocarbon emulsions;
4:o ethyl ester results in metabolic properties other than those obtained with triglyceride ester.

It has also been surprisingly found in the case of many substances that, in addition to the aforementioned advantages, these esters are better solvents than triglycerides of animal or vegetable origin. The technique of dissolving pharmacologically active substances in triglycerides, such as soyabean oil, and subsequently preparing the solution to emulsion form with the aid of suitable emulsifiers is known to the art, (for instance from U.S. application Ser. No. 4,168,308). It has been found, however, that in many cases the solubility of these substances in such oils is so poor that desired concentrations in the final emulsion cannot be reached. It has now surprisingly been found that the solvent properties of these alkyl esters, for instance ethyl esters of fatty acids, are totally different from the solvent properties of the triglyceride esters present in the fatty acids animal and vegetable origins. The use, for instance, of fatty acid ethyl esters enables oil-in-water emulsions to be prepared which contain higher quantities of pharmacologically active substances in the hydrophobic phase. The particle size of these emulsions will also be smaller than the particle size of the emulsions based on triglyceride. Since the particles in an alkyl-ester emulsion are much smaller than the particle size of conventional fat emulsions, there is obtained a much greater specific diffusion surface area, thereby resulting in a more rapid and more powerful effect of the active substance.

According to one important embodiment of the invention, the present emulsion will thus contain one or more pharmacologically active substances dissolved or dispersed in the hydrophobic phase. These substances, or agents, may be of very different types, as will be made apparent in the following, and the type of active substance is used is not intended to limit the scope of the present invention.

Furthermore, the inventive emulsions may contain X-ray contrast agents, particularly in the form of one or more iodized fats or contrast substances for such investigative procedures as computer tomography and NMRI (Nuclear Magnetic Resonance Imaging). These substances or agents may be present in a quantity of 1-60 percent by weight, calculated on the whole emulsion.

It will also be apparent that the inventive emulsion has two essential areas of use. The first of these areas is the use of the emulsion as a nutrient source intended for parenteral nutrient supply. The second of said areas is the use of the emulsion as a vehicle for carrying pharmacologically active substances, including X-ray contrast substances or media, these substances being dissolved or dispersed in the hydrophobic phase. The afore-illustrated advantages are thus achieved by the superior solvent properties and solution promoting properties of the ingoing alkyl esters. It will be understood, however, that the two areas of use may also be combined, such that an emulsion intended for nutrient supply can include one or more pharmacologically active substances in the hydrophobic phase.

The inventive emulsions are primarily intended for intravenous administration, particularly when used for nutrient supply. The emulsions, however, can also be administered parenterally in any other manner, the manner in which the emulsions are administered being determined by the effect and function of the pharmacologically active substances included and by the indications or symptoms of the patient.

The compositions prepared in accordance with the invention may also contain various additives, i.e. in addition to the active substances (or substances) and the hydrophilic component, comprising water, optionally with substances dissolved therein, and the hydrophobic component, comprising alkyl esters, and then particularly ethyl esters of fatty acids. There further additives may, for instances, comprise preserving agents, pH-adjusters and agents for achieving a suitable osmotic pressure. In this respect, one of the most important additives will comprise one or more suitable emulsifiers capable of providing a stable dispersion. A multiple of emulsifying and suspension agents of both natural and synthetic origin can be used in this respect. Examples of such agents include phospholipids deriving from eggs or soyabeans, and polyethylene and polypropylene glycols. Many useable emulsifiers are known from the literature and are commercially available, and the person skilled in this particular art will have no problem in selecting one or more agents suitable for the purpose intended.

The emulsion may also contain nutrients dissolved or dispersed in the aqueous phase. Examples of such substances include, for instance, amino acids, glycerol, glucose, fructose, xylitol, sorbitol or other sugars or alcohols, water-soluble vitamins, salts and trace elements. The emulsion may contain several of these substances at one and the same time. Furthermore, the aqueous phase may also contain water-soluble, pharmacologically active substances.

All of the particles present in an inventive emulsion will have a diameter considerably smaller than 1 micron, thereby obviating the risk of the particles fastening in the capillaries. An emulsion having a particle size of 0.1-0.3 micron can be produced without any great difficulty. This renders the system stable. It has also been found that the inventive emulsions can be prepared in a manner to prevent the particles from forming agglomerates in the blood. The inventive emulsions will withstand being autoclaved and can be stored for long periods without degredation or decomposition. Furthermore, it has been found that the actual vehicle system is well tolerated and will not result in secondary effects, when administered intravenously.

An example of pharmacologically active substances capable of being administered in accordance with the present invention include those which belong to one of the following groups:

| Centrally active substances: | |
|---|---|
| such as | active depressants |
| | anaesthetics |
| | active anagelsics |
| | central stimulants |
| Substances having peripheral effect on the neuromuscular system: | |
| such as | spasmolytics |
| | muscle relaxing substances |
| Substances which affect the cardiac and vascular system: | |
| such as | substances having a vasopressor effect |
| Substances which affect the respiratory system: | |
| such as | asthma treating substances |

Contrast substances for use in conventional radiology diagnosis, datortomographic and NMRI (Nuclear Magnetic Resonance Imaging) investigations.

Antiobiotic, cytostatic and chemotherapeutical substances.

The list of such substances is indefinite.

Emulsions prepared in accordance with the present invention exhibit a high degree of tolerance in experiments carried out on animals. Ethyl esters of fatty acids obtained from soyabean oil have been examined in infusion experiments on rats. In this respect it was possible to administer 70 ml/kg intravenously at a rate of 0.3 ml/kg/min without the occurrence secondary effects. The volume used corresponded approximately to the energy consumed each minute by the animal concerned. Subsequent to hydrolysis of the ethyl esters, the amount of alcohol administered to the animals in the aforesaid experiments corresponds to only 10% of the total energy requirement of the body. This supply of alcohol has no appreciable physiological or medicinal significance. In other experiments, rats were given repeated daily infusions of the aforesaid 10%-ethyl-ester emulsion in an amount of 150 ml/kg over a planned trial period of 14 days. No secondary effects were observed. The animals exhibited a normal weight increase. The amount administered exceeded 40% of the energy requirement of the animals.

The emulsion itself was prepared in a conventional manner, i.e. a manner well known to the skilled person from, for instance, the aforecited literature. Thus, the hydrophobic phase, the emulsifier and the aqueous phase can be mixed together to form a "coarse emulsion", which is then homogenized in some suitable apparatus to a suitable particle size with regard to the hydrophobic phase. Those substances intended to be in solution or dispersion in the hydrophobic phase, and/or the aqueous phase are normally first dissolved in respective phases prior to mixing said phases together. Subsequent to homogenization, the emulsion is poured into suitable containers and then sterilized.

As will be understood, it is imperative that the quality of the emulsion ingredients is such as to be free from pharmacological complaint, and that this quality is sustained through the whole of the process of preparation. Thus, the components must be free from contaminants capable of causing harmful secondary effects, such as pyrogens, and must also be protected from the harmful effect, for instance, of oxidation, prior to, during and subsequent to the process of preparation, all of which is well known to the person skilled in this art.

The invention will now be described with reference to a number of examples.

EXAMPLE 1

100 g of soyabean oil were mixed with 1 liter of absolute alcohol. It was found that the oil did not dissolve, but lay in a layer beneath the alcohol. Sodium alcoholate was then added in an amount corresponding to 0.25 g metallic sodium. A clear solution was obtained after 20-30 minutes, subsequent to trans-esterification of the soyabean oil taking place. Three volumes of water were added and the resultant oil layer was then isolated and washed with some small volumes of water. The resultant oil comprised the ethyl esters of the fatty acids of the soyabean oil.

The viscosity of the ethyl esters is significantly lower than the viscosity of the original soyabean oil. The specific weight is also lower than the specific weight of corresponding triglyceride.

50 g of the ethyl esters were mixed with 6 g phospholipids, 12.5 g glycerol and water to a volume of 500 ml. 1 M NaOH was added to obtain a pH between 7 and 10.5, whereafter the mixture was homogenized in a conventional manner, e.g. in a Moulin-Gaulin homogenizer. The resultant emulsion was heat sterilized at 120° C. for 20 minutes. Subsequent to being analyzed for control purposes, the emulsion was ready for intravenous administration. The measured particle size was 0.15-0.30 micron.

The emulsion was administered in quantities of 150 ml per kilogram and day to rats under a planned 14 day course of administration. The rats exhibited a good increase in weight. No signs of secondary effects were observed. The amount administered corresponded to about 40 to 50% of the energy requirements of the rats.

EXAMPLE 2

100 g of oil (soyabean oil, safflower oil, olive oil or some other vegetable or animal oil) were mixed with 2 liters of 0.2 M NaOH and 0.5 liter of hexane while slowly stirring the mixture. The hexane fraction was separated, subsequent to all fat having been saponified. The aqueous solution was neutralized with 1 liter of 0.5 M HCl. The resultant layer of free fatty acids was separated and washed with water. Subsequent to having removed all water with water-free sodium sulphate, the fatty acids were esterified with ethyl alcohol or some other alkyl alcohol in a manner similar to that described, for instance, by C. H. Rogers (A method for manufacturing oenanthylate. J. Amer. Pharmaceut. Assoc. Sci. Ed. Vol 12:503-506, No. 6, 1923.)

The esters obtained were used to prepare fat emulsion. The ingredients used were as follows:

| Ethyl esters of fatty acids | 100 g |
| --- | --- |
| Egg yolk phospholipid | 12 g |
| Glycerol | 25 g |

Sterile and pyrogen-free water to an amount of 1000 ml Sodium hydroxide solution 1 M in an amount sufficient to obtain a pH of 7-10.5.

The ingredients were mixed in a Turmix, Turrax or a similar mixer. The resultant "coarse emulsion" was homogenized in an homogenizer of the type Moulin-Gaulin microfluidizer or the like. The emulsion obtained was sterilized in an autoclave at 120° C. for 20 minutes.

EXAMPLE 3

Ethyl esters of fatty acids obtained from animal or vegetable fat were mixed with phospholipids from eggs or soyabean oil and glycerol in the following proportions:

| Ethyl esters of fatty acids | 100 g |
| --- | --- |
| Phopholipids | 12 g |
| Glycerol | 22.5 g |

These ingredients were thoroughly mixed in a Turmix or Turrax apparatus or like mixers. Sterile and pyrogen-free water was then added to the mixture to a total volume of 1000 ml. The emulsion obtained will be sterile, provided that the emulsion is prepared from sterile and pyrogen-free ingredients under aseptic conditions. When this is not the case, the emulsion can be heat sterilized. This methodology will provide an emulsion of desirable particle size.

EXAMPLE 4

Diazepam was dissolved in ethyl esters of fatty acids obtained from animal or vegetable fat, and an emulsion was prepared from the solution. The ingredients were used in the following proportions:

| Diazepam | 0.5 g |
| --- | --- |
| Ethyl ester | 10 g |
| Phospholipid from eggs | 1.2 g |
| Glycerol | 2.25 g |
| Sterile and pyrogen-free water to | 100 ml |
| Sodium hydroxide solution 1M to pH | 7-10.5 |

The emulsion was poured into bottles of desired volume and the emulsion then heat sterilized at 120° C.

The diazepam/ethyl-ester emulsion of this example was compared with a diazepam/soyabean emulsion with regard to creaming in vitro with plasma and serum derived from seriously ill patients under intensive care. The method by which creaming is determined is given in Swedish Patent Application No. 8505047-4 filed 25 Oct. 1985. The results obtained are set forth in Tables 1 and 2 below. It will be seen from the results that the creaming activity decreased dramatically (i.e. the creaming time had increased) when ethyl ester was used as the hydrophobic phase in diazepam-containing emulsions, instead of soy-oil.

TABLE 1

Investigations concerning the creaming of diazepam/ethyl-ester emulsion and diazepam/soy-oil emulsion. The tests were carried out with serum deriving from patients under intensive care.

| Patient | Creaming times (hours) of diazepam emulsions containing: | |
|---|---|---|
| | Soyoil | Ethyl ester |
| 497 S-G | ½ | 7 |
| 499 H | ½ | >24 |
| 486 H | ½ | >24 |
| 501 H | 1 | >24 |
| 505 S-G | 1 | >24 |
| 498 H | 2 | >24 |
| 499 H | 2 | >24 |
| 500 H | 2 | >24 |
| 502 S-G | 2 | 24 |
| 506 S-G | 2 | 24 |
| 488 K-G | 3 | >24 |
| 495 S-G | 3 | >24 |
| 503 S-G | 3 | >24 |
| 507 S-G | 3 | >24 |
| 494 S-G | 4 | >24 |
| 496 S-G | 4 | >24 |

TABLE 2

Investigations concerning the creaming of diazepam/ethyl ester emulsion and diazepam/soy-oil emulsion The tests were carried out with plasma deriving from patients under intensive care.

| Patient | Creaming time (hours) of diazepam emulsion the hydrophobic part of which comprised: | |
|---|---|---|
| | Soy-oil | Ethyl ester |
| 497 S-G | ½ | 4 |
| 506 S-G | ½ | 7 |
| 486 H | ½ | >24 |
| 499 H | ½ | >24 |
| 500 H | ½ | >24 |
| 507 S-G | 1 | 24 |
| 502 S-G | 1 | 24 |
| 501 H | 1 | >24 |
| 505 S-G | 1 | >24 |
| 488 K-S | 2 | >24 |
| 494 S-G | 2 | >24 |
| 495 S-G | 2 | >24 |
| 498 H | 2 | >24 |
| 496 S-G | 3 | >24 |
| 503 S-G | 3 | >24 |
| 490 K-S | 5 | >24 |
| 487 K-S | 5 | >24 |
| 491 S-G | 6 | >24 |

EXAMPLE 5

An emulsion was prepared from the following ingredients:

| Pregnenolone | 600 mg |
|---|---|
| Ethyl ester of fatty acids obtained from animal or vegetable fat | 20 g |
| Phospholipid from egg | 1.2 g |
| Glycerol | 2.5 g |
| Sterile and pyrogen-free water to a quantity of | 100 ml |
| Sodium hydroxide solution 1M to pH | 7–10.5 |

Homogenization was effected in the same manner as that described in Example 2. The emulsion was poured into bottles and heat sterilised at 120° C. for 20 minutes.

EXAMPLE 6

| Iodized soyabean oil | 30 ml |
|---|---|
| Ethyl ester of fatty acid obtained from soyabean oil | 10 ml |
| Phenylalanine | 0.2 g |
| Phospholipid from eggs | 2.0 g |
| Glycerol | 2.25 g |
| Sterile and pyrogen-free water to an amount of | 100 ml |
| Sodium hydroxide solution 1M to pH | 7.5–10 |

The mixture was homogenized in the same manner as that described in Example 2 and the emulsion was poured into bottles and then heat sterilized at 120° C. for 20 minutes.

The particle size of the emulsion was determined in a conventional manner and found to lie between 0.15–0.20 micron.

EXAMPLE 7

Amphotericin B is an antifungal antibiotic. The substance is soluble in dimethyl acetamide and dimethylsulfoxide, but very difficult to dissolve in water and common organic solvents. An infusion suspension can be prepared with sodium deoxycholate. This suspension, however, is highly unstable and must therefore be used within 8 hours from the time of its preparation. It has now been found that a stable emulsion having the following composition can be prepared when ethyl ester from vegetable oil is used as a solution promotor.

| Amphotericin B | 75 mg |
|---|---|
| Ethyl ester of fatty acids from soyabean oil | 15 g |
| Soyabean oil | 22.5 g |
| Phospholipid from eggs | 3.37 g |
| Glycerol | 6.75 g |
| Sterile and pyrogen-free water to an amount of | 300 ml |
| Sodium hydroxide solution 1M to pH | 7.5–10 |

The emulsion was prepared and sterilized in the same way as that described in Example 2.

EXAMPLE 8

| Perfluorodecalin (Flutec PP5 from ISC Chemicals Ltd.) | 28 g |
|---|---|
| Ethyl ester of fatty acids from soyabean oil | 10 g |
| Phospholipid from eggs | 1.2 g |
| Glycerol | 2.5 g |
| Sterile and pyrogen-free water to an amount of | 100 ml |
| Sodium hydroxide solution 1M to pH | 7–10 |

The emulsion was prepared and sterilized in the same manner as that described in Example 2.

What is claimed is:

1. An emulsion for parenteral administration comprising a hydrophobic phase as a vehicle for carrying pharmacologically active agent emulsified in an aqueous phase, one or more emulsifying agents in an amount sufficient to emulsify said hydrophobic phase in said aqueous phase, at least one lipophilic pharmacologically active agent in a pharmacologically effective amount, wherein said emulsifying agent comprises a phospholipid from eggs or soybeans, the emulsion has a particle size from 0.1 to 0.3 μm, and that the hydrophobic phase comprises one or more ethyl esters of pharmacologically acceptable fatty acids of soybean oil, and wherein the ethyl ester content of the emulsion is from 5 to 60 percent by weight.

2. The emulsion according to claim 1 wherein the hydrophobic phase also includes glyceryl esters of fatty acids, the weight ratio of ethyl esters to glyceryl esters being from 10:1 to 1:10.

3. The emulsion according to claim 1 wherein the aqueous phase of the emulsion also contains at least one member selected from the group consisting of glycerol, fructose, xylitol and sorbitol.

4. The emulsion according to claim 1 wherein at least one lipophilic pharmacologically active agent is selected from the group consisting of active depressants, anaesthetics, analgesics, central stimulants, spasmolytics, muscle relaxing substances, substances which affect the cardiac and vascular system, substances which affect the respiratory system, contrast substances for X-ray or NMRI investigations, antibiotics, cytostatics and chemotherapeutics.

5. The emulsion according to claim 1 wherein the emulsion has dissolved or dispersed in the ethyl esters at least one member selected from the group consisting of iodized fat, iodized fatty acid alkyl ester, and perfluorocarbon compound in an amount of from 1–60 percent by weight.

6. The emulsion according to claim 1 which comprises ethyl esters of fatty acids.

7. The emulsion according to claim 1 wherein the ethyl ester content of the emulsion is from 5 to 30 percent by weight.

8. The emulsion according to claim 2 wherein the aqueous phase of the emulsion also contains at least one member selected from the group consisting of glycerol, fructose, xylitol and sorbitol.

9. The emulsion according to claim 2 wherein at least one lipophilic pharmacologically active agent is selected from the group consisting of active depressants, anaesthetics, analgesics, central stimulants, spasmolytics, muscle relaxing substances, substances which affect the cardiac and vascular system, substances which affect the respiratory system, contrast substances for X-ray or NMRI investigations, antibiotics, cytostatics and chemotherapeutics.

10. The emulsion according to claim 2 wherein the emulsion has dissolved or dispersed in the ethyl esters at least one member selected from the group consisting of iodized fat, iodized fatty acid alkyl ester, and perfluorocarbon compound in an amount of from 1–60 percent by weight.

11. The emulsion according to claim 2 which comprises ethyl esters of fatty acids.

12. The emulsion according to claim 2 wherein the ethyl ester content of the emulsion is from 5 to 30 percent by weight.

13. The emulsion according to claim 5 wherein the ethyl ester content of the emulsion is from 5 to 30 percent by weight.

* * * * *